United States Patent [19]
Hartigan et al.

[11] 4,089,331
[45] May 16, 1978

[54] SURGICAL DRAPE WITH FENESTRATION LINER

[75] Inventors: Edward G. Hartigan, Acton, Mass.; Donald Patience, Barrington, Ill.

[73] Assignee: The Kendall Company, Boston, Mass.

[21] Appl. No.: 747,583

[22] Filed: Dec. 6, 1976

[51] Int. Cl.² ............................................. A61B 19/06
[52] U.S. Cl. ................................................ 128/132 D
[58] Field of Search ........................... 128/132 D, 292

[56] References Cited

U.S. PATENT DOCUMENTS

| | | | |
|---|---|---|---|
| 3,503,391 | 3/1970 | Melges | 128/132 D |
| 3,791,382 | 2/1974 | Collins | 128/132 D |
| 3,871,369 | 3/1975 | Krzewinski | 128/132 D |
| 3,910,268 | 10/1975 | Miller | 128/132 D |
| 4,033,341 | 7/1977 | Scrivens | 128/132 D |

*Primary Examiner*—Lawrence W. Trapp
*Attorney, Agent, or Firm*—Powell L. Sprunger

[57] ABSTRACT

A surgical drape comprising, a sheet of flexible material resistant to the passage of bacteria for covering a portion of a patient's body, with the covering sheet having a fenestration for placement over a surgical site. The drape has an auxiliary sheet of flexible material resistant to the passage of body fluids connected to the drape and extending a sufficient distance past an edge of the fenestration for placement of an end portion in a surgical incision to isolate the surgical site and control runoff of fluids.

11 Claims, 3 Drawing Figures

U.S. Patent May 16, 1978 4,089,331
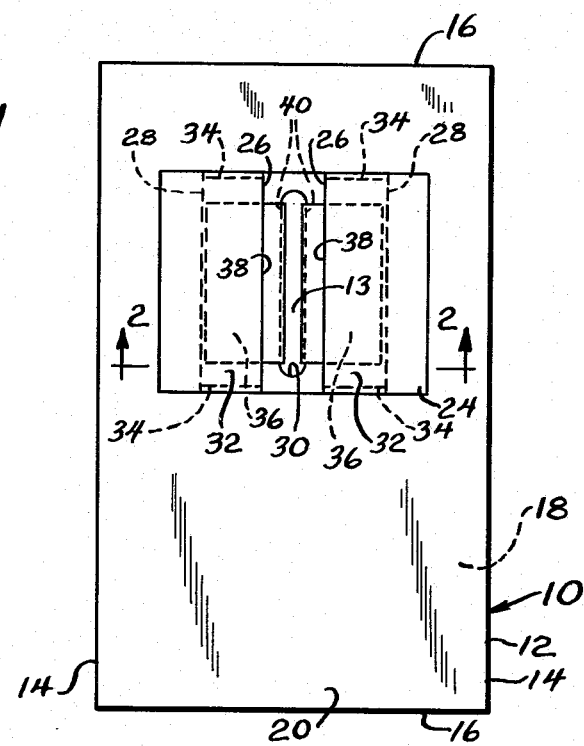
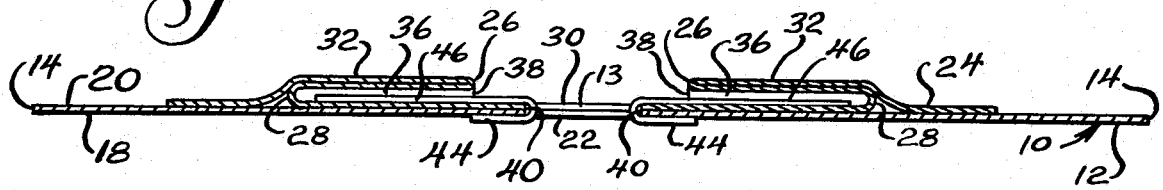
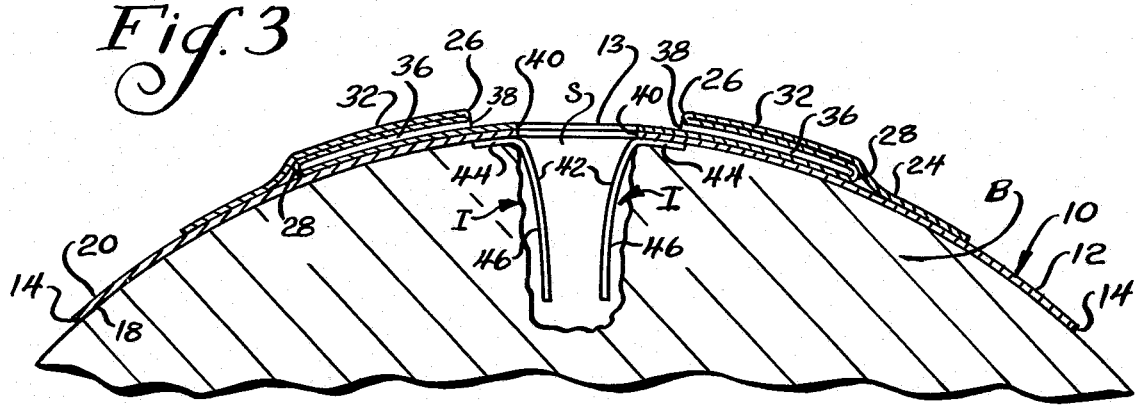

SURGICAL DRAPE WITH FENESTRATION LINER

BACKGROUND OF THE INVENTION

The present invention relates to surgical articles, and more particularly to surgical drapes.

Before the present invention, a various assortment of surgical drapes have been proposed for use during an operation. Such drapes are normally constructed with a sterile main sheet of flexible material which is resistant to passage of bacteria and body fluids. The main sheet is placed over a patient with a fenestration in the sheet located over a surgical site, and the operation is performed through the fenestration. The main sheet is intended to serve as a barrier between the patient's body and operating room personnel in a region around the surgical site, and thus prevent contamination to the patient's body. However, due to the irregular contour of the patient's body, it has been found that the drapes frequently do not conform to the shape of the body, thus causing formation of gaps between the fenestration edges and the patient's body adjacent the surgical site. As a result, the surgical site is not isolated from the remainder of the patient's body, which increases the possibility of contamination to the site. Moreover, the gaps permit runoff of body fluids from the site between the drape and patient's body.

SUMMARY OF THE INVENTION

A principal feature of the present invention is the provision of a surgical drape of simplified construction for isolating a surgical site from the remainder of the patient's body.

The drape of the present invention comprises, a sheet of flexible material resistant to the passage of bacteria for covering a portion of the patient's body, with the covering sheet having a fenestration for placement over the surgical site. The drape has an auxiliary sheet of flexible material resistant to the passage of body fluids connected to the drape and extending a sufficient distance past an edge of the fenestration for placement of an end portion in a surgical incision at the site.

A feature of the present invention is that the placed end portion of the auxiliary sheet isolates the surgical site and minimizes the possibility of contamination to the site.

Another feature of the invention is that the end portion of the auxiliary sheet controls the runoff of body fluids and minimizes the possibility of fluid runoff passing between the drape and the patient's body.

A feature of the present invention is that the auxiliary sheet may be stored at a location overlying an outer surface of the drape, and may be moved to an operative position in the surgical incision after placement of the drape.

Yet another feature of the invention is that the drape may include a pocket member adjacent the fenestration, and the end portion of the auxiliary sheet may be stored in the pocket member prior to use of the drape.

Still another feature of the invention is that the auxiliary sheet controls the runoff of body fluids into the pocket member for retention therein.

Further features will become more fully apparent in the following description of the embodiments of this invention and from the appended claims.

DESCRIPTION OF THE DRAWINGS

In the drawings:

FIG. 1 is a front plan view of a surgical drape of the present invention;

FIG. 2 is a sectional view taken substantially as indicated along the line 2—2 of FIG. 1; and FIG. 3 is a sectional view of the drape in position on a patient with liners of the drape positioned in a surgical incision.

DESCRIPTION OF THE PREFERRED EMBODIMENTS

Referring now to FIGS. 1 and 2, there is shown a sterile surgical drape generally designated 10 having a main sheet 12 for placement over a patient's body, and a fenestration 13 through which an operation is performed. Although the drape of the present invention may be constructed for use in many suitable operations, for convenience the drape is illustrated in a form which may be utilized during a laparotomy procedure. As shown, the main sheet 12 has a pair of side edges 14, a pair of end edges 16 connecting the side edges 14, an inner surface 18 facing toward the patient after placement of the drape, and an outer surface 20 facing away from the patient after placement of the drape. The main sheet also has an elongated fenestration 22 for placement over a surgical site on the patient. The main sheet 12 may be made from any suitable flexible material which is resistant to passage of bacteria and body fluids, such as a nonwoven material treated to provide fluid repellency.

In a preferred form, the drape 10 has a reinforcement sheet 24 secured to the outer surface 20 of the main sheet 12 with a fenestration 30 in the reinforcement sheet 24 being aligned with the fenestration 22 of the main sheet 12 in order to define the elongated fenestration 13 of the drape 10. As shown, the reinforcement sheet 24 has a pair of first longitudinally extending fold lines 26 adjacent opposed peripheral edges 40 of the fenestration 13, and a pair of second longitudinally extending fold lines 28 located intermediate the fold lines 26 and respective side edges 14 of the main sheet 12 on opposed sides of the fenestration 13, such that the fold lines 26 and 28 define a pair of opposed pocket members 32 on the outer surface of the drape 10. The sides of the pocket members 32 are secured together by suitable means, such as lines 34 of adhesive, in order to define pockets 36 in the pocket members 32 with openings 38 of the pocket members 32 communicating with the pockets 36 and facing toward the peripheral edges 40 of the fenestration 13 on opposed sides of the drape fenestration 13. Thus, the pocket members are located adjacent opposed sides of the drape fenestration 13 to capture fluid runoff from the surgical site during use of the drape.

The drape 10 also has a pair of opposed auxiliary sheets or liners 42 secured to the drape adjacent the drape fenestration 13. In a preferred form, as shown, one end 44 of each liner 42 is secured to the inner surface 18 of the main sheet 12 adjacent a respective opposed peripheral edge 40 of the drape fenestration 13. Also, as shown, the liners 42 are folded around the respective fenestration edges 40, and the other end portions 46 of the liners 42 may be located in the pockets 36 of the pocket members 32. The liners 42 may be made of any suitable flexible material which is resistant to passage of bacteria and body fluids, such as a nonwoven material which is treated to provide fluid repellency. However, in a preferred form, the liners 42 are impervious to passage of body fluids and bacteria and are made from a transparent plastic material, such as polyvinylchloride. As shown in FIG. 1, the liners 42 may extend substantially the length of the elongated fenestration edges 40. In the configuration of FIGS. 1 and 2, the end portions 46 of the liners 42 are located in the pockets 36 of the pocket members 32, and the liners are thus suitably retained in a storage position in the pocket members 32 preparatory to use. Alternatively, in the absence of the pocket members 30, the end portions 46 of the liners 42 may be folded against the outer surface 20 of the drape 10 in a suitable storage position prior to use of the drape.

In use, with reference to FIG. 3, the drape 10 is placed over the patient's body B with the drape fenestration 13 being located over the surgical site S preparatory to the operation. After an incision I has been made in the patient's body, the end portions 46 of the liners 42 may be removed from the pocket members 32 and passed through the drape fenestration 13 into the surgical incision I. In this configuration, the liners 42 serve as a barrier along the walls of the surgical incision I, and thus isolate the surgical site S from the remaining portion of the patient's body in order to minimize the possibility of contamination to the surgical site S. Also, the liners 42 control the runoff of body fluids from the surgical site S and direct and runoff through the openings 38 into the pockets 36 of the pocket members 32 for retention therein. As previously indicated, the liners 42 are preferably transparent, in order that the walls of the incision I may be observed through the liners 42 during the operation.

Thus, in accordance with the present invention, the drape 10 has a pair of opposed liners which may be retained in a storage position on an outer surface of the drape, and preferably, in a pair of opposed pocket members. After a surgical incision has been made in the patient, the liners may be unfolded from the storage position in the pocket members, and are passed through the drape fenestration to an operative position lining the walls of the surgical incision. In this configuration, the liners minimize the possibility of contamination to the surgical site, and control runoff of body fluids from the surgical site into the pocket members while preventing passage of the fluids between the drape and the patient's body. Of course, the liners may be retained in their storage position in the pocket members throughout the operation, if desired for a particular surgical procedure.

The foregoing detailed description is given for clearness of understanding only, and no unnecessary limitations should be understood therefrom, as modifications will be obvious to those skilled in the art.

We claim:

1. A surgical drape comprising, a sheet of flexible material resistant to the passage of bacteria for covering a portion of a patient's body, with the covering sheet having a fenestration for placement over a surgical site, and said drape having an auxiliary sheet of flexible material resistant to the passage of body fluids and bacteria connected to the drape and extending a sufficient distance past an edge of the fenestration for placement of an end portion in a surgical incision to isolate the surgical site and control runoff of fluids, said drape including a pocket member having an opening facing toward said fenestration edge, with the end portion of said auxiliary sheet being selectively positioned in the pocket member.

2. The drape of claim 1 wherein the auxiliary sheet is secured to the drape at a location adjacent the fenestration edge.

3. The drape of claim 1 wherein said auxiliary sheet is made from a plastic material.

4. The drape of claim 3 wherein said auxiliary sheet is transparent.

5. A surgical drape comprising, an outer surface facing away from a patient after placement of the drape, an inner surface facing toward the patient after placement of the drape, edges defining the periphery of the drape, a fenestration spaced from said peripheral edges of the drape for placement over a surgical site and having a pair of opposed elongated peripheral edges, and a pair of opposed flexible liners connected to the drape adjacent a respective peripheral edge of the fenestration, said liners being movable between a storage position overlying said outer surface and extending away from the respective fenestration edge, and an operative position with end portions of the liners extending from the respective fenestration edge into a surgical incision, said liner end portions being free of adhesive.

6. The drape of claim 5 wherein said liners are secured to the inner surface of the drape.

7. The drape of claim 5 wherein said liners extend substantially the length of said edges.

8. The drape of claim 5 wherein said drape includes a pair of opposed pocket members adjacent the opposed fenestration edges and having openings facing toward the respective fenestration edge.

9. The drape of claim 8 wherein said liners are received in the respective pocket member in said storage position.

10. The drape of claim 1 wherein the length of said auxiliary sheet is greater than half the width of said fenestration.

11. The drape of claim 5 wherein the length of said liners is greater than half the width of said fenestration.

* * * * *